United States Patent [19]

Kita et al.

[11] Patent Number: 5,093,363
[45] Date of Patent: Mar. 3, 1992

[54] 2,4,6-SUBSTITUTED PHENOL DERIVATIVES

[75] Inventors: Toru Kita, Kyoto; Hiroshi Harada, Toyonaka; Eiichi Ohsugi, Kawanishi; Toshiro Konoike, Suita, all of Japan

[73] Assignee: Shionogi & Co., Ltd., Osaka, Japan

[21] Appl. No.: 567,158

[22] Filed: Aug. 14, 1990

[30] Foreign Application Priority Data

Aug. 22, 1989 [JP] Japan .................................. 1-216647

[51] Int. Cl.$^5$ .................. A61K 31/19; A61K 31/235; C07C 323/52
[52] U.S. Cl. .................................. 514/532; 514/570; 560/17; 560/60; 562/431; 562/470; 549/375; 549/292
[58] Field of Search .................... 549/292; 560/17, 60; 562/431, 470; 514/532, 570

[56] References Cited

U.S. PATENT DOCUMENTS

| | | | |
|---|---|---|---|
| 4,029,812 | 6/1977 | Wagner et al. | |
| 4,076,841 | 2/1978 | Wagner et al. | |
| 4,078,084 | 3/1978 | Wagner et al. | |
| 4,248,889 | 2/1981 | Oka et al. | 560/60 |
| 4,609,673 | 9/1986 | Eggerer et al. | 514/542 |
| 4,645,854 | 2/1987 | Verhoeven et al. | 560/60 |
| 4,711,903 | 12/1987 | Mueller et al. | 560/17 |
| 4,801,611 | 1/1989 | Chinn et al. | 514/532 |
| 4,898,868 | 2/1990 | Bergmann et al. | 514/277 |

FOREIGN PATENT DOCUMENTS 0127848 12/1984 European Pat. Off. .
0273451 7/1988 European Pat. Off. .

OTHER PUBLICATIONS

H. Nakaya, Farumashia, 24, 1217, (1988).
Probucol, The Merck Index, 11th Ed., pp. 1230, 7761.

Primary Examiner—Nicky Chan
Attorney, Agent, or Firm—Birch, Stewart, Kolasch & Birch

[57] ABSTRACT

A 2,4,6-substituted phenol having the formula (I):

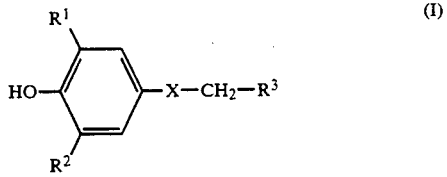

wherein X is S or $CH_2$; $R^1$ and $R^2$ are the same or different from each other and each is a lower alkyl group; $R^3$ is a group of the formula:

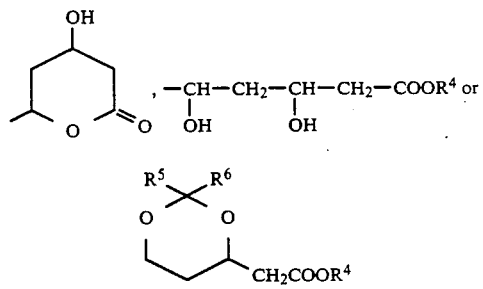

in which $R^4$ is hydrogen atom or a lower alkyl group; $R^5$ and $R^6$ are the same or different from each other and each is hydrogen atom, a lower alkyl group, or a phenyl group which may be substituted, or a pharmaceutically acceptable salt thereof is useful as an active agent in a pharmaceutical composition. The pharmaceutical composition comprises a therapeutically effective amount of a compound having the formula (I), as an effective ingredient, in association with a pharmaceutically acceptable substantially nontoxic carrier or excipient. The pharmaceutical composition can be useful in the treatment of lipemia of mammals. Additionally the compounds can be used as antiatherosclerotic agents and antilipenic agents.

8 Claims, No Drawings

2,4,6-SUBSTITUTED PHENOL DERIVATIVES

BACKGROUND OF THE INVENTION

The present invention relates to a 2,4,6-substituted phenol derivatives which can be utilized in the medical field. More particularly, the present invention relates to a 2,4,6-substituted phenol having both HMG-CoA (3-hydroxy-3-methylglutaryl coenzyme A) reductase inhibitory activity and antioxidation action. The derivatives are useful as antiatherosclerotic agents, antilipemic agents and agents for preventing the progress of arteriosclerosis. Besides, the above-mentioned 2,4,6-substituted phenols have inhibitory action on ulcer formation and the like relating to antioxidation action and antiinflammatory action and the like relating to action for preventing cytotoxicity and lipoxygenase inhibitory action. Accordingly, the substituted phenol derivatives can be used as an antiangiopathic agent, an antiasthmatic agent, an antidiabetic agent, an antiulcer agent, an antiinflammatory agent, an antineoplastic agent, an antiallergic agent or the like.

Atherosclerosis is regarded to be the incipient process of arteriosclerosis which is caused by depositing lipids containing cholesterol as a primary component in intimae of aortas and arteries, hyperplasia of arterial walls in company with the deposition and hyperplasia of connective tissue, and hardening.

Factors relating to the onset of atherosclerosis are never simple. Until now, hypertension, lipemia, excessive smoking, obesity, diabetes, hyperuricemia, stress, heredity, lack of exercise and the like have been exemplified, as dangerous factors of atherosclerosis. It is considered that atherosclerosis is caused by piling these dangerous factors for a long time. Among them, behavior of cholesterol which exists as LDL in blood is particularly noticed. In particular, accumulation of cholesterol on arterial walls resulting from incorporation of the oxidized LDL into macrophages in arterial walls is important. The resulting accumulation causes angiopathy. On the other hand, it has been considered that development of atherosclerosis is accelerated by various factors such as increase of cholesterol in blood in association with disturbance in incorporation of LDL into liver and cacochymia of LDL in liver, hydrodynamic condition of blood in association with physical change of blood and red blood cell, damage of endothelial cells, physiological or pathologic hypertrophy of arterial walls and decrease in utilization of lipids in tissue of arteries.

Hitherto, in drug therapy of atherosclerosis, antiatherosclerotic agents such as pyridinol carbamate, agents for lowering lipids, such as clofibrate, nicotinic acid, α-thyroxine and cholestyramin, and inhibitory agents on platelet aggregation, such as dipyridamole and aspirin, have been used as agents relating to such complicated.

There are two methods of interest in lowering the lipids content in serum. The first method is preventing the oxidation and denaturation of LDL. In this method, compounds having a structure of 2,4,6-substituted phenol are used. Such compounds are, for instance, disclosed in U.S. Pat. Nos. 4,029,812, 4,076,841, 4,078,084, European Patent No 273451 and the like. The second method utilizes the inhibitory action of HMG-CoA CoA reductase. This method which comprises inhibiting the biosynthesis of cholesterol from acetic acid in the body is considered to be effective against the onset of atherosclerosis and in therapy of atherosclerosis. Nakatani discloses that Mevastatin, Pravastatin, Lovastatin and Simarastatin inhibit cholesterol synthesis, and suggests the posibility that a compound having HMG-CoA reductase inhibitory activity can be applied as an antiarterioscelorotic agent and an antilipemic agent (See Farmashia, Kusuri no kaisetsu, HMG-CoA reductase inhibitor, 24, number 12, pages 1217–1219, 1988).

As is clear from the above description, it is considered that inhibition of cholesterol synthesis and cholesterol incorporation into macrophages by preventing oxidation and denaturation of LDL are important for prevention and treatment of atherosclerosis. The development of medicaments useful in both of the above described methods has been desired.

As the result of the continuous effort of the present inventors, they have designed a 2,4,6-substituted phenol having both antioxidation activity and HMG-CoA reductase inhibitory activity. The present invention is based upon these finding.

As structurally similar compounds to the compound of the present invention, those described in U.S. Pat. No. 4,801,611, Japanese Unexamined Patent Publication No. 6653/1985, Japanese Unexamined Patent Publication No. 158164/1985 and Japanese Unexamined Patent Publication No. 38086/1989, and Probucol having the formula:

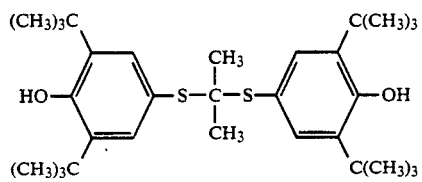

are exemplified. However, there is no satisfiable compound having both antioxidation activity and simultaneously, HMG-CoA reductase inhibitory activity as the compounds of the present invention exhibit.

It is an object of the present invention to provide a 2,4,6-substituted phenol having both antioxidation activity and HMG-CoA reductase inhibitory activity at the same time or a pharmaceutically acceptable salt thereof.

A further object of the present invention is to provide a pharmaceutical composition comprising the same or a pharmaceutically acceptable salt thereof as an effective ingredient, in association with a pharmaceutically acceptable substantially nontoxic carrier or excipient.

It is a still further object of the present invention to provide a useful pharmaceutical composition for lipemia comprising the same or a pharmaceutically acceptable salt thereof.

These and the other objects of the present invention will become apparent from the description hereinafter.

SUMMARY OF THE INVENTION

In accordance with the present invention, there are provided 2,4,6-substituted phenols having the formula (I):

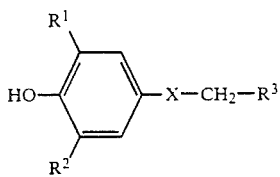

(I)

wherein X is S or CH₂; R¹ and R² are the same or different from each other and each is a lower alkyl group; R³ is a group of the formula:

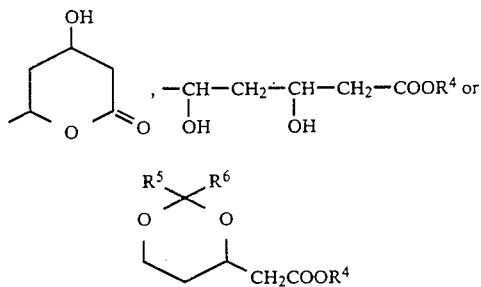

in which R⁴ is hydrogen atom or a lower alkyl group;
R⁵ and R⁶ are the same or different from each other and each is hydrogen atom, a lower alkyl group, or a phenyl group which may be substituted, or a pharmaceutically acceptable salt thereof; a pharmaceutical composition comprising a therapeutically effective amount of a compound having the formula (I), as an effective ingredient, in association with a pharmaceutically acceptable substantially nontoxic carrier or excipient and a pharmaceutical composition for use in the treatment of lipemia of mammals (human, animals) comprising a therapeutically effective amount of at least one compound having the formula (I).

In the specification of the present invention, the term "a lower alkyl" means a straight chain or branched chain alkyl having 1-8 carbon atoms. Examples of the lower alkyl are, for instance, methyl, ethyl, propyl, isopropyl, n-butyl, isobutyl, sec-butyl, tert-butyl, 1-methylpropyl, n-pentyl, isopentyl, neopentyl, tert-pentyl, 1-methylbutyl, 2-methylbutyl, 1,1-dimethylpropyl, 1,1-dimethylbutyl, 2,2-dimethylbutyl, n-hexyl, isohexyl, heptyl, octyl and the like. Preferably the term "a lower alkyl" means a straight chain or branched chain alkyl having 1-6 carbon atoms. Examples of the preferable lower alkyl are, for instance, methyl, ethyl, propyl, isopropyl, n-butyl, isobutyl, sec-butyl, tert-butyl, 1-methylpropyl, n-pentyl, isopentyl, neopentyl, tert-pentyl, 1-methylbutyl, 2-methylbutyl, 1,1-dimethylpropyl, 1,1-dimethylbutyl, 2,2-dimethylbutyl, n-hexyl, isohexyl and the like.

Especially preferable lower alkyl of R¹ and R² is a branched chain alkyl. Examples of the lower alkyl of R¹ and R² are, for instance, isopropyl, isobutyl, sec-butyl, tert-butyl, 1-methylpropyl, isopentyl, neopentyl, tert-pentyl, 1-methylbutyl, 2-methylbutyl, 1,1-dimethylpropyl, 1,1-dimethylbutyl, 2,2-dimethylbutyl, isohexyl and the like.

Especially preferable lower alkyl of R₄ is a straight chain or branched chain alkyl having 1-4 carbon atoms. Examples of the lower alkyl of R⁴ are, for instance, methyl, ethyl, propyl, isopropyl, n-butyl, isobutyl, sec-butyl, tert-butyl and the like.

Examples of "a phenyl which may be substituted" are phenyl, p-methoxyphenyl, 2,4-dimethoxyphenyl, p-dimethylaminophenyl, o-nitrophenyl and the like.

The compounds of the present invention prepared in the working examples are optically active substances. However, the present invention contains all stereoisomers or a mixture represented by the formula (I). The compound (I) of the present invention can form a salt with an alkali metal such as lithium, sodium or potassium, an alkaline earth metal such as calcium, ammonia, an amino acid such as lysine or arginine, an organic amine such as triethylamine or dicyclohexylamine, and the like.

DETAILED DESCRIPTION

The compound (I) of the present invention can be prepared according to the following description.

That is, the compound (I) of the present invention wherein X is S can be prepared by reacting the compound having the formula (II):

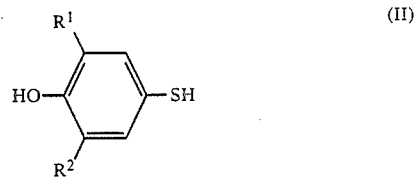

wherein R¹ and R² are as defined above, with an alkylating agent having the formula (III):

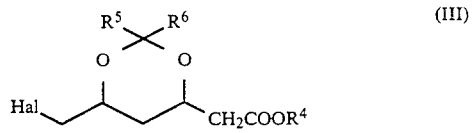

wherein Hal is a halogen atom, R⁴, R⁵ and R⁶ are as defined above, if necessary, by subjecting to deprotection, lactonization and/or salt formation.

In the above present reaction, the compound (II) and the compound (III) can be prepared according to a well-known sulfide synthesis method.

The present reaction can be carried out in the presence of a basic substance such as sodium hydroxide, potassium hydroxide, calcium hydroxide, potassium carbonate, pyridine, 4-dimethylaminopyridine or triethylamine in a solvent such as an alcohol solvent, for instance, methanol, ethanol, propanol, tert-butanol or the like, an ether solvent, for instance, diethyl ether, tetrahydrofuran or the like, N,N-dimethylacetamide, N,N-dimethylformamide or acetonitrile, with cooling or at room temperature, or under reflux for 10 minutes to several tens hours. In case that the present reaction is carried out in a solvent immiscible with the basic substance, for instance, when the basic substance such as a salt with an alkali hydroxide or a salt with an alkali carbonate is reacted in a solvent such as an alcohol solvent, for instance, methanol, ethanol, propanol, tert-butanol or the like, a halogenated hydrocarbon, for instance, dichloromethane, chloroform, dichloroethane or the like or an aromatic solvent, for instance, benzene, toluene or the like, the reaction may be carried out in the presence of a phase-transfer catalyst such as tetra-n-butyl-ammonium iodide in a system of said solvent alone or a two layer system of water and said solvent.

Deprotection can be carried out by acid hydrolysis or catalytic reduction according to a conventional method However, the acid hydrolysis is general. Tendency to be hydrolyzed depends on kind of substituents, glycol and the like. The reaction can be carried out by using an acid such as hydrochloric acid, sulfuric acid, acetic acid or trifluoroacetic acid in a solvent, for instance, a halogenated hydrocarbon such as chloroform or dichloromethane, an alcohol solvent such as ethanol or methanol, an ether solvent such as dioxane, tetrahydrofuran or diethylether, if necessary, water is mixed with the above solvent and a mixture is used as a solvent, with cooling or at room temperature, or under reflux for several tens minutes to several hours.

The yielded hydroxycarboxylic acid is automatically cyclized to be a lactone. Such reaction is remarkably accelerated by an inorganic acid as well as the esterification of a carboxylic acid with an alcohol.

The salt formation is carried out as below. A lactone is hydrolyzed by using a base such as an alkali hydroxide, for instance, lithium hydroxide, potassium hydroxide, sodium hydroxide, barium hydroxide or the like in a mixed solvent of water and a water-soluble solvent, for instance, an alcohol solvent such as ethanol or methanol, an ether solvent such as dioxane, tetrahydrofuran or diethylether, or acetonitrile, or the like with cooling or at room temperature, or under reflux according to a conventional method. Then, the hydrolyzed product is treated with an acid such as nitrous acid, formic acid, acetic acid, propionic acid, butyric acid, acrylic acid, benzoic acid, oxalic acid, succinic acid, tartaric acid or citric acid to give a free hydroxycarboxylic acid. After once the obtained hydroxycarboxylic acid is extracted with a suitable solvent and isolated, the hydroxycarboxylic acid is treated with the desired basic substance, for instance, an alkali hydroxide such as lithium hydroxide, potassium hydroxide, sodium hydroxide or calcium hydroxide, ammonia, an amino acid such as lysine or arginine, an organic amine such as triethylamine or dicyclohexylamine, or the like with cooling or at room temperature, or under reflux according to a conventional method to give a carboxylate.

The compound (I) of the present invention wherein X is $CH_2$ can be prepared according to the following description.

That is, the compound of the present invention having the formula (V):

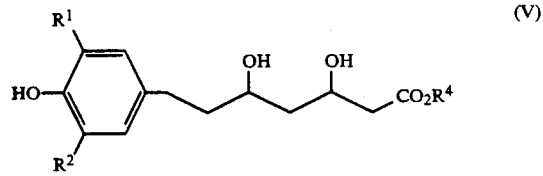

(V)

wherein $R^1$, $R^2$ and $R^4$ are as defined above, can be prepared by reducing the compound having the formula (IV):

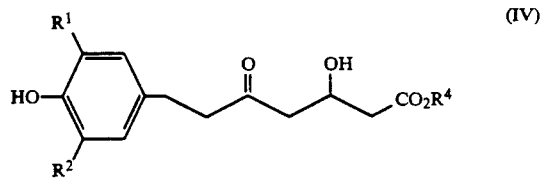

(IV)

wherein $R^1$, $R^2$ and $R^4$ are as defined above, if necessary, the compound (I) of the present invention wherein X is $CH_2$ can be prepared by subjecting the compound (V) of the present invention to salt formation or lactonization.

The present reaction can be carried out in a solvent such as an alcohol solvent, for instance, methanol, ethanol, propanol, tert-butanol or the like, an ether solvent, for instance, diethyl ether, tetrahydrofuran or the like, N,N-dimethylacetamide, N,N-dimethylformamide or acetonitrile, in the presence of a boron compound such as diethyl methoxy borane, diethyl ethoxy borane or tri-n-butyl borane, by using a reducing agent such as sodium borohydride, zinc borohydride or K-or L-Selectride, with cooling or at room temperature, or under reflux for few minutes to several hours.

The salt formation can be carried out as follows. A ester is hydrolyzed by base such as alkali metal hydroxide, for instance lithium hydroxide potassium hydroxide, sodium hydroxide, or the like in a mixed solvent of water and water-soluble solvent, for instance, ethanol, methanol, tetrahydrofurane with cooling or at room temperature, or under refluxing conditions.

Or alternatively a salt is prepared by consecutive acidification and treatment by a base. The hydrolyzate is treated with an acid such as nitrous acid, formic acid, acetic acid, propionic acid, butyric acid, acrylic acid, benzoic acid, oxalic acid, succinic acid, tartaric acid or citric acid to give a free hydroxycarboxylic acid. After once the obtained hydroxycarboxylic acid is extracted with a suitable solvent and isolated, the hydroxycarboxylic acid is treated with the desired basic substance, for instance, an alkali hydroxide such as lithium hydroxide, potassium hydroxide, sodium hydroxide or calcium hydroxide, ammonia, an amino acid such as lysine or arginine, an organic amine such as triethylamine or dicyclohexylamine, or the like with cooling or at room temperature, or under reflux according to a conventional method to give a carboxylate.

The lactonization can be carried out as follows. An ester is lactonized by an acid such as p-toluenesulfonic acid, hydrochloric acid, trifluoromethansulfonic acid, boron trifluoridediethyl ether, in a solvent such as toluene, dichloromethane, tetrahydrofuran with azeotropic removal of generated alcohol with cooling, or at room temperature or under reflux.

Also, the compound having the formula (IV) can be prepared according to the following description.

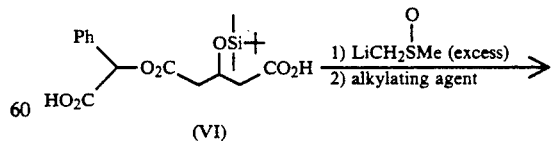

(VI)

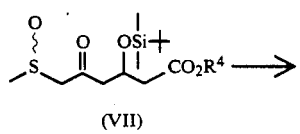

(VII)

-continued

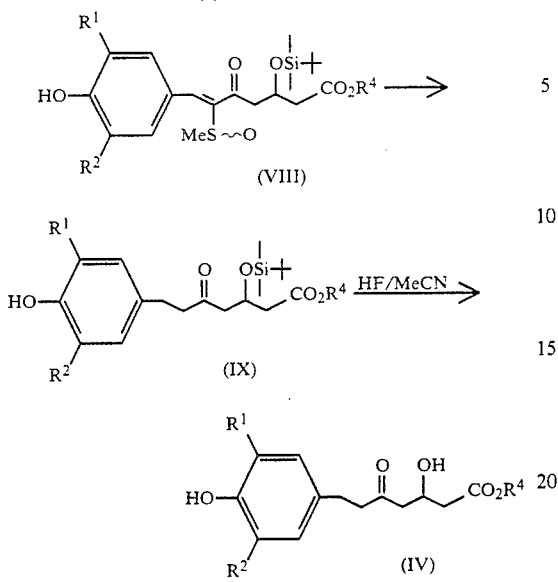

In the above reaction formula, $R^1$, $R^2$ and $R^4$ are as defined above.

The compound having the formula (VII) can be prepared by adding excess lithium salt of dimethylsulfoxide, sodium salt of dimethylsulfoxide, or methylsulfinylmethyl lithium to the compound (VI) and then by reacting with an alkylating agent such as diazomethane, dimethylsulfate or alkyl halide, e.g., iodo methane.

Further, the compound having the formula (VIII) can be prepared by reacting the compound (VII) with the compound (XI) produced according to the following reaction formula in the presence of base such as lithium bis-trimethylsilylamido, sodium hydride or 1,8-diazabicyclo[5.4.0]undec-7-ene.

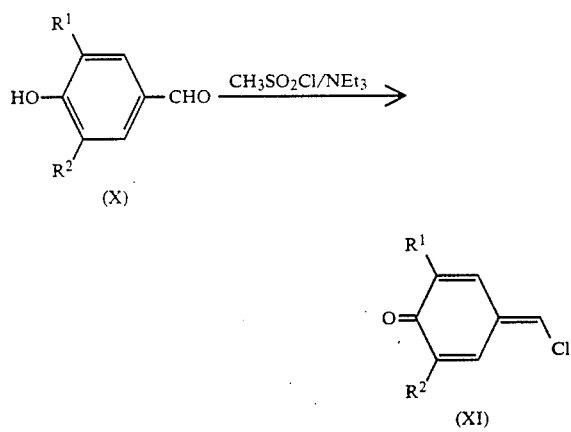

In the above reaction formula, $R^1$ and $R^2$ are as defined above.

The compound (IX) can be obtained by reducing the obtained compound (VIII) with, for instance, Raney nickel, sodium amalgam, palladium on carbon or the like.

Furthermore, the compound (IV) can be obtained according to deprotion of the compound (IX) by a conventional method using an acid such as hydrogen fluoride, aqueous hydrochloric acid or tetra-n-butyl ammonium fluoride.

Also, the compound having the formula (VI) can be obtained by cleaving 3-(tert-butyldimethylsilyloxy)-glutaric anhydride with benzylester of L-mandelic acid in an atmosphere of nitrogen, then reducing the reaction product with palladium hydroxide (See Japanese Patent Application No. 314028/1989).

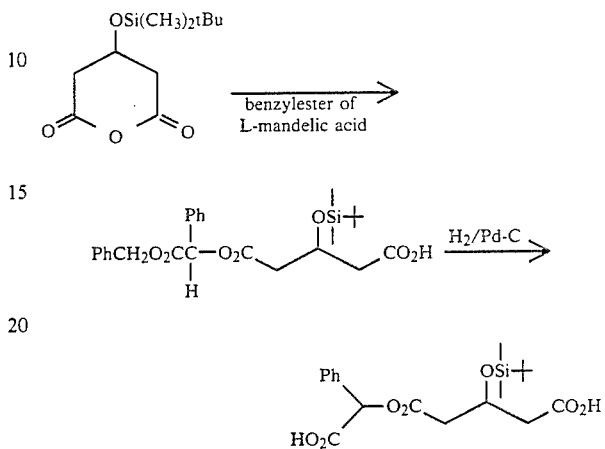

The compound having the formula (I) of the present invention prepared in this way can be isolated and collected by well-known means of separation and purification such as chromatography, crystallization, and the like.

The compound of the present invention can be orally or parenterally administered. In case of oral administration, the compound of the present invention can be used in any form of a general preparation, for instance, a solid preparation such as tablets, powders, capsules or granules, a liquid preparation such as aqueous or oily suspension, syrups or elixirs, or the like. In case of parenteral administration, the compound of the present invention can be used in an aqueous or oily suspending injection composition. In preparing these composition carriers or excipients, including any of the vehicles, binders, lubricants, aqueous solvents, oily solvents, emulsifiers, suspending agents and the like, that are normally employed can be used. Examples of the carrier or excipient include crystalline cellulose, gelatin, lactose, starch, magnesium stearate, talc, vegetable or animal fats or oils, gums and polyalkylene glycol and the like. Also, other additives such as preservatives and stabilizers may be contained in such preparations. The pharmaceutical composition of the present invention can contain another pharmaceutical ingredient such as another antilipemic agent compatible with the pharmaceutical composition of the present invention. In this case, the compound of the present invention is not necessarily a main ingredient of the preparation.

Though the dosage of the compound (I) of the present invention is different according to route of administration, age, body weight, condition and a kind of disease of a patients, in oral administration, usual dosage of the compound (I) of the present invention is in the range of 5 to 1000 mg, preferably in the range of 20 to 200 mg for day for an adult, in parenteral administration, usual dosage of the compound (I) of the present invention is in the range of 1 to 500 mg, preferably in the range of 5 to 50 mg per day for an adult. The administration of the dosage may be devided into 1 to 5 times.

The present invention is more specifically described and explained by means of the following Reference Examples, Examples and Test Examples in which all per cents and parts are by weight unless otherwise noted. It is to be understood that the present invention is not limited to the Reference Examples, the Examples and the Test Examples, and various changes and modifications may be made in the invention without departing from the spirit and scope thereof.

REFERENCE EXAMPLE 1

[tert-Butyl [(4R,6S)-6-(iodomethyl)-2,2-dimethyl-1,3-dioxane-4-yl]acetate]

To a solution containing 36.71 g (0.274 mol) of methyl (3S)-3,4-dihydroxybutylate (Japanese Unexamined Patent Publication No. 22056/1988), 55.39 g (0.546 mol) of triethylamine, 1.67 g (0.013 mol) of 4-N,N-dimethylaminopyridine and 275 m: of dry methylene chloride was added dropwise 78.99 g (0.287 mol) of tert-butylchlorodiphenylsilane with stirring and cooling with ice. After reacting the mixture for 4 hours, the mixture was allowed to stand for two days and two nights at $-20°$ C. Methylene chloride was distilled away under reduced pressure. To the residue was added ether, insoluble matters were filtered off. Further after washing with water and drying, ether solution was distilled away under reduced pressure. The obtained oily residue was purified by subjecting to silica gel column chromatography [eluent: hexane-ethyl acetate (8:1 to 3:1 by volume, hereinafter the same)]to give 87.82 g of methyl (3S)-4-tert-butyldiphenylsilyloxy-3-hydroxybutylate as syrups (yield: 86%).

$^1$H-NMR spectrum (in CDCl$_3$) δ ppm:
7.75–7.60 (4H, m), 7.50–7.33 (6H, m),
4.25–4.10 (1H, m), 3.69 (3H, s),
3.73–3.57 (2H, m), 2.89 (1H, b),
2.65–2.45 (2H, m), 1.07 (9H, s)

To a solution containing 45.79 g (0.452 mol) of diisopropyl amine and 350 ml of anhydrous tetrahydrofuran was added dropwise 303.35 ml (0.452 mol) of hexane solution containing 1.49 M butyllithium at $-30°$ to $-20°$ C. with stirring and the mixture was reacted for a half hour at the same temperature. The reaction solution was cooled to $-70°$ C., and thereto was added dropwise a solution containing 52.50 g (0.452 mol) of tert-butylacetate and 50 ml of anhydrous tetrahydrofuran with stirring. After stirring the mixture for 1 hour at $-70°$ to $-65°$ C., thereto was added dropwise a solution containing 42.15 g (0.113 mol) of methyl (3S)-4-tert-butyldiphenylsilyloxy-3-hydroxybutylate and 45 ml of anhydrous tetrahydrofuran at $-60°$ to $-50°$ C. After stirring the mixture for a half hour at $-50°$ C., further for 5 hours at $-40°$ to $-30°$ C., into the reactant was poured a solution of 500 ml of saturated aqueous solution of ammonium chloride and 500 ml of water at a temperature not more than $-5°$ C. After stirring for a half hour, the mixture was extracted with ether. The ether layer was washed with water, then dried and distilled away under reduced pressure to give 60 g of the residue as oil. The residue was purified by subjecting to silica gel column chromatography [eluent: hexane-ether (3:2)]to give 49.04 g of tert-butyl (5S)-6-tert-butyldiphenylsilyloxy-5-hydroxy-3-oxohexanoate as syrups (yield: 95%).

$^1$H-NMR spectrum (in CDCl$_3$) δ ppm: 7.70–7.60 (4H, m), 7.50–7.33 (6H, m),
4.30–4.14 (1H, m), 3.66 (1H, dd, J=10.0, 4.4 Hz), 3.60 (1H, dd, J=10.0, 6.0 Hz),
3.39 (2H, s), 2.82 (1H, d, J=4.0 Hz),
2.72 (2H, d, J=6.2 Hz), 1.46 (9H, s),
1.06 (9H, s)

To a solution containing 52.53 g (0.115 mol) of tert-butyl (5S)-6-tert-butyldiphenylsilyloxy-5-hydroxy-3-oxohexanoate, 800 ml of anhydrous tetrahydrofuran and 200 ml of anhydrous methanol was added 126 ml (0.126 mol) of a 1 M solution of diethyl methoxy borane in tetrahydrofuran with stirring at $-70°$ C. After stirring the mixture for 1 hour at $-65°$ C., thereto was added 5.66 g (0.15 mol) of sodium borohydride and the mixture was reacted for 4 hours at the same temperature. The reactant was added dropwise to the mixture of 425 ml of 30% hydrogen peroxide, 850 ml of 0.2 M phosphate buffer solution (pH 7.0 ) and 850 ml of methanol at $-20°$ to $-10°$ C. Further after stirring the mixture for a half hour at room temperature, the mixture was concentrated under reduced pressure. The concentrated solution was extracted with methylene chloride, and the methylene chloride layer was washed with water, then dried and distilled away under reduced pressure. The residue was purified by subjecting to silica gel column chromatography [eluent: methylene chloride-ethyl acetate (10:1)]to give 40.1 g of tert-butyl (3R,5S)-6-tert-butyldiphenylsilyloxy-3,5-dihydroxyhexanoate as syrups (yield: 75%).

$^1$H-NMR spectrum (in d6 -DMSO) δ ppm: 7.70–7.60 (4H, m), 7.50–7.36 (6H, m),
4.69 (2H, d, J=5.3 Hz), 4.12–3.92 (1H, m),
3.80–3.63 (1H, m), 3.55 (1H, dd, J=10.0, 4.8 Hz), 3.46 (1H, dd, J=10.0, 5.8 Hz),
2.34 (1H, dd, J=14.4, 5.1 Hz), 2.20 (1H, dd, J=14.4, 8.0 Hz), 1.80–1.30 (2H, m),
1.38 (9H, s), 0.9 (9H, s)
$[α]_D^{24}$: $-10.2±0.5°$ (c=1.036, methanol)

To a solution containing 40.0 g (0.0872 mol) of tert-butyl (3R,5S)-6-tert-butyldiphenylsilyloxy-3,5-dihydroxyhexanoate, 36.32 g (0.349 mol) of 2,2-dimethoxypropane and 50 ml of anhydrous methylene chloride was added 0.882 g (3.49 mmol) of pyridinium p-toluenesulfonate, and the mixture was stirred for 5.3 hours at room temperature. To the reaction solution was added 88 ml of saturated solution of sodium hydrogencarbonate. After stirring for a half hour at room temperature, the mixture was extracted with ether. The solution extracted with ether was washed with water, then dried and distilled away under reduced pressure to give 43 g of a residue as syrups. The residue was purified by subjecting to silica gel column chromatography [eluent: hexane-ether (3:2)] to give 36.45 g of tert-butyl [(4R,6S)-6-[(tert-butyldiphenylsilyloxy) methyl]-2,2-dimethyl-1,3-dioxane-4-yl]acetate as syrups (yield: 84%).

$^1$H-NMR spectrum (in CDCl$_3$) δ ppm: 0 7.72–7.63 (4H, m), 7.47–7.30 (6H, m),
4.35–4.18 (1H, m), 4.06–3.90 (1H, m),
3.71 (1H, dd, J=10.2, 5.2 Hz), 3.53 (1H, dd, J=10.2, 6.2 Hz), 2.44 (1H, dd, J=15.0, 7.2 Hz),
2.30 (1H, dd, J=15.0, 6.0 Hz),
1.75–1.0 (2H, m), 1.45 (9H, s), 1.43 (3H, s),
1.35 (3H, s), 1.05 (9H, s)
$[α]_D^{24}$: $-4.4±0.4°$ (c=1.039, methanol)

To a solution of 100 ml of anhydrous tetrahydrofuran containing 12.13 g (0.0243 mol) of tert-butyl [(4R,6S)-6-[(tert-butyldiphenylsilyloxy)methyl]-2,2-dimethyl-1,3-dioxane-4-yl]acetate was added 26.75 ml (0.0268 mol) of the 1 M solution of tetrabutylammonium fluoride in tetrahydrofuran with stirring at −15° C. and reacted for 2.5 hours at 0° to 5° C. The reaction solution was subjected to 120 g of silica gel column chromatography and eluted with ethyl acetate, and the eluate was collected and distilled away under reduced pressure. Again the residue was subjected to silica gel column chromatography and eluted [eluent: methylene chloride-acetonitrile (4:1)]. The first fraction was discarded and successive elution gave 5.52 g of tert-butyl [(4R,6S)-6-(hydroxymethyl)-2,2-dimethyl-1,3-dioxane-4-yl]acetate as syrups (yield: 87%).

$^1$H-NMR spectrum (in CDCl$_3$) δ ppm:
4.39–4.22 (1H, m), 4.10–3.94 (1H, m),
3.70–3.43 (1H, m), 2.46 (1H, dd, J=15.2, 7.0 Hz), 2.31 (1H, dd, J=15.2, 6.2 Hz),
1.99 (1H, dd, J=7.0, 5.6 Hz),
1.56–1.22 (2H, m), 1.48 (3H, s),
1.45 (9H, s), 1.39 (3H, s)
$[\alpha]_D^{24}$: −5.7±0.4° (c=1.080, methanol)

To a solution of 1.0 g (3.84 mmol) of tert-butyl [(4R,6S)-6-(hydroxymethyl)-2,2-dimethyl-1,3-dioxane-4-yl]acetate, 2.01 g (7.68 mmol) of triphenylphosphine, 0.523 g (7.68 mmol) of imidazole and 11.5 ml of anhydrous benzene was added 1.46 g (5.8 mmol) of iodine with stirring and cooling with ice, and then reacted for 2.5 hours at room temperature. The deposited crystal was filtered, and the obtained crystal was washed with ether. The filtrate and the washings were combined and distilled away under reduced pressure. The residue was purified by subjecting to silica gel column chromatography [eluent: hexane-methylene chloride (1:1), successively ethyl acetate-methylene chloride (1:9)]to give 1.41 g of tert-butyl [(4R,6S)-6-(iodomethyl)-2,2-dimethyl-1,3-dioxane-4-yl]acetate as syrups (yield: 99%).

$^1$H-NMR spectrum (in CDCl$_3$) δ ppm:
4.35–4.18 (1H, m), 3.96–3.80 (1H, m),
3.17 (1H, dd, J=10.0, 5.8 Hz), 3.09 (1H, dd, J=10.0, 6.2 Hz), 2.46 (1H, dd, J=15.2, 7.2 Hz),
2.32 (1H, dd, J=15.2, 6.2 Hz), 1.87 (1H, dt, J=12.8, 2.4 Hz), 1.45 (12H, s), 1.40 (3H, s),
1.15 (1H, dd, J=12.6, 11.6 Hz)

REFERENCE EXAMPLE 2

[(3R)-Methyl 7-(3,5-di-tert-butyl-4-hydroxy)phenyl-3-hydroxy-5-oxohexanoate]

To a suspension of 120 ml of methylene chloride containing 24.3 g (0.1 mol) of 3,5-di-tert-butyl-4-hydroxybenzaldehyde hemihydrate were added dropwise 27.8 ml (0.2 mol) of triethylamine and 15.5 ml (0.2 mol) of methanesulfonyl chloride successively. After the reaction mixture was refluxed with heating for 6 hours, the reaction mixture was poured into ice-cold water and extracted with methylene chloride. The methylene chloride layer was washed with diluted hydrochloric acid, a solution of sodium hydrogencarbonate and a brine solution. After drying over anhydrous magnesium sulfate, the layer was concentrated to give 48.0 g of 4-chloromethylene-2,6-di-tert-butyl-2,5-cyclohexadiene-1-one (yield: 95%).

$^1$H-NMR spectrum (in CDCl$_3$) δ ppm: 1.28 (9H, s), 1.32 (9H, s), 6.8–6.9 (2H, m),
7.42 (1H, dd, J=2.4, 0.6 Hz)

$^{13}$C-NMR spectrum (in CDCl$_3$) δ ppm: 29.45, 29.49, 35.11, 35.66, 125.26, 130.73, 130.93, 133.67, 147.83, 150.70, 186.98

IR (in CHCl$_3$) cm$^{-1}$: 2958, 1613, 1535, 1361, 1252, 844

To a mixture of 270 ml of THF and 25.6 m; (0.36 mol) of dimethyl sulfoxide (DMSO) was added 168 ml of a solution of hexane containing 1.6N n-butyllithium at −30° C. After stirring the mixture for 20 minutes, thereto was added dropwise 120 ml of a solution of THF containing 23.79 g of hydrogen (3S,1'S)-1-(1'-carboxy-1'-phenyl)ethyl-3-(tert-butyldimethylsilyl)oxy pentanedioate at −70° C. Temperature of the mixture was increased gradually, and the mixture was stirred for 30 minutes at −15° C. Then, the mixture was poured into diluted hydrochloric acid and extracted with methylene chloride. An organic layer was washed with diluted hydrochloric acid and a brine solution and dried over anhydrous magnesium sulfate to give a solution of crude carboxylic acid. The solution was subjected to TLC [developing solvent: chloroform-methanol (3:1)], and Rf value thereof was 0.8. To a solution of crude carboxylic acid was added ca. 1% solution of diazomethane in diethyl ether at −20° C. until yellow color of diazomethane was sustained. After the solution of obtained methyl ester was concentrated, the residue was purified by subjecting to silica gel column chromatography [eluent: acetone-ethyl acetate (1:1)]and collecting eluate to give 14.43 g of (3R)-methyl 3-(tert-butyldimethylsilyloxy)-6-methylsulfinyl-5-oxohexanoate (yield: 71%). Rf value thereof was 0.3 (ethyl acetate). NMR spectrum of obtained (3R)-methyl 3-(tert-butyldimethylsilyloxy)-6-methylsulfinyl-5-oxohexanoate, shows a mixture of two diastereoisomer of the sulfoxide.

$^1$H-NMR spectrum in CDCl$_3$ δ ppm: 0.07 (3H, s), 0.09 (3H, s), 0.85 (9H, s),
2.5–2.6 (2H, m), 2.7 (3H, s), 2.8–3.0 (2H, m),
3.68 (3H, s), 3.7–3.9 (2H, m), 4.5–4.7 (1H, m)

To a solution of 102 ml of THF containing 10.22 g (30.4 mmol) of (3R)-methyl 3-(tert-butyldimethylsilyloxy)-6-methylsulfinyl-5-oxohexanoate obtained according to the above-mentioned method was added dropwise 33 ml of 1 M lithium bis-(trimethylsilyl)-amido at −78° C. Thereto was added 8.45 g (33.4 mmol) of 4-chloromethylene-2,6-di-tert-butyl-2,5-cyclohexadiene-1-one prepared separately. The reaction mixture was stirred for 2 hours at room temperature, and was poured into the ice cooled mixture of ethyl acetate and diluted hydrochloric acid and extracted with ethyl acetate. An organic layer was washed with water. After drying with anhydrous magnesium sulfate, the organic layer was concentrated. The residue was purified by subjecting to silica gel column chromatography [eluent: n-hexane-ethylacetate (1:1), then ethylacetate-acetone (1:1)] to give 8.19 g of (3R)-methyl 3-(tert-butyldimethylsilyl)oxy-7-(3,5-di-tert-butyl-4-hydroxy)phenyl-6-methylsulfinyl-5-oxo-6-heptenoate (yield: 49%) and 3.23 g of the starting compound (3R)-methyl 3-(tert-butyldimethylsilyloxy)-6-methylsulfinyl-5-oxohexanoate (yield: 32%). The yielded compound was a mixture of at least two kinds of isomer. Rf value of the yielded compound was 0.7 (hexane-ethyl acetate (1:1)).

$^1$H-NMR spectrum (in CDCl$_3$) δ ppm:
0.64, 0.10, 0.13 (6H, s), 0.88, 0.91 (9H, s),
1.57, 1.59 (18H, s), 2.5–3.1 (4H, m),
2.93 (3H, s), 3.74, 3.75 (3H, s),
4.5–4.7 (1H, m), 6.78 (1H, s),
7.34, 7.36, 7.34 (2H, s), 7.74, 7.78 (1H, s)

To a solution of 80 ml of dioxane containing 11.67 g (21.1 mmol) of (3R)-methyl-3-(tert-butyldimethylsilyl)oxy-7-(3,5-di-tert-butyl-4-hydroxy)phenyl-6-methylsulfinyl-5-oxo-6-heptenoate obtained according to the above-mentioned method was added about 50 g of Raney nickel, and the mixture was stirred for 1 hour at 90° C. Raney nickel was filtered off. The filtrate was concentrated and then purified by subjecting to silica gel column chromatography [eluent: n-hexane-ethylacetate (2:1)] to give 8.08 g of (3R)-methyl 3-(tert-butyldimethylsilyl)oxy-7-(3,5-di-tert-butyl-4-hydroxy)phenyl-5-oxo-heptanoate (yield: 75%). Rf value thereof was 0.6 (hexane-ethyl acetate (2:1)).

$^1$H-NMR spectrum (in CDCl$_3$) δ ppm: 0.04 (3H, s), 0.07 (3H, s), 0.84 (9H, s), 1.42 (18H, s), 2.4-2.8 (8H, m), 3.66 (3H, s), 4.5-4.7 (1H, m), 5.06 (1H, s), 6.96 (2H, s), 7.26 (1H, s)

$^{13}$C-NMR spectrum (in CDCl$_3$) δ ppm: −4.99, −4.81, 17.91, 25.76, 29.53, 30.37, 34.37, 42.44, 46.62, 50.10, 51.61, 66.03, 125.10, 131.74, 136.27, 152.44, 171.85, 208.90

$[α]_D^{25}$: −1.82° (c=3.47, CHCl$_3$)

IR (film) cm$^{-1}$: 3645, 2950, 1736, 1712, 1433, 1250, 1193, 835, 776

After 8.81 g (17.2 mmol) of (3R)-methyl 3-(tert-butyldimethylsilyl)oxy-7-(3,5-di-tert-butyl-4-hydroxy)phenyl-5-oxo-heptanoate obtained according to the above-mentioned method was treated with 57 ml of acetonitrile and 3 ml of 46% HF for 2.5 hours, the mixture was poured into a solution of sodium hydrogencarbonate and extracted with ethyl acetate. An organic layer was washed with water, dried with anhydrous magnesium sulfate and then concentrated. The residue was purified by subjecting to silica gel column chromatography [eluent: n-hexane-ethyl acetate (2:1)] to give 5.91 g of (3R)-methyl-7-(3,5-di-tert-butyl-4-hydroxy)phenyl-3-hydroxy-5-oxo-hexanoate (yield: 91%). Rf value thereof was 0.5 (hexane-ethyl acetate (2:1)).

$^1$H-NMR spectrum (in CDCl$_3$) δ ppm: 1.43 (18H, s), 2.5-2.9 (8H, m), 3.71 (3H, s), 4.4-4.6 (1H, m), 5.08 (1H, s), 6.96 (2H, s)

EXAMPLE 1

[tert-Butyl [(4R,6S)-6-[[(3,5-di-tert-butyl-4-hydroxyphenyl)thio]methyl]-2,2-dimethyl-1,3-dioxane-4-yl]acetate]

A mixture of 0.12 g (0.324 mmol) of tert-butyl [(4R,6S)-6-(iodomethyl)-2,2-dimethyl-1,3-dioxane-4-yl]acetate, 0.0925 g (0.388 mmol) of 2,6-di-tert-butyl-4-mercaptophenol (See R. J. Laufer, U.S. Pat. No. 3,129,262), 0.067 g (0.49 mmol) of powderly anhydrous potassium carbonate and 0.5 ml of dry N,N-dimethylformamide was stirred for 16 hours at room temperature. The reaction solution was distilled away under reduced pressure. The residue was dissolved in ether, washed with saturated brine solution, dried and distilled away under reduced pressure. The residue was purified by subjecting to silica gel column chromatography [eluent: ethyl acetate-methylene chloride (1:19)]]to give 0.143 g of tert-butyl [(4R,6S)-6-[[(3,5-di-tert-butyl-4-hydroxyphenyl)thio]methyl]-2,2-dimethyl-1,3-dioxane-4-yl]acetate as crystals (yield: 92%). The desired compound was recrystallized from hexane.

mp: 102°-103° C.

$^1$H-NMR spectrum (in CDCl$_3$) δ ppm: 7.24 (2H, s), 5.20 (1H, s), 4.32-4.16 (1H, m), 4.06-3.90 (1H, m), 3.00 (1H, dd, J=13.2, 6.0 Hz), 2.79 (1H, dd, J=13.2, 6.6 Hz), 2.44 (1H, dd, J=15.2, 7.2 Hz), 2.30 (1H, dd, J=15.2, 6.0 Hz), 1.81 (1H, dt, J=12.6, 2.6 Hz), 1.44 (3H, s), 1.43 (27H, s), 1.39 (3H, s), 1.20 (1H, q, J=12.8 Hz)

$[α]_D^{24}$: −7.3±0.5° (c=1.010, methanol)

Elemental analysis value: As C$_{27}$H$_{44}$O$_5$S

Calculated C: 67.46, H: 9.22, S: 6.67

Found C: 67.35, H: 9.22, S: 6.64

EXAMPLE 2

[(4R,6S)-6-[[(3,5-Di-tert-butyl-4-hydroxyphenyl)thio]methyl]-4-hydroxytetrahydropyrane-2-one]

In 6.5 ml of anhydrous methylene chloride was dissolved 0.647 g (1.346 mmol) of tert-butyl [(4R,6S)-6-[[(3,5-di-tert-butyl-4-hydroxyphenyl)thio]methyl]-2,2-dimethyl-1,3-dioxane-4-yl]acetate. Thereto was added dropwise 1.3 ml of trifluoroacetic acid with cooling with ice and stirred for a half hour at the same temperature, further stirred for 2 hours at room temperature. The reaction solution was distilled away under reduced pressure. To the residue was added toluene, and again the mixture was distilled away under reduced pressure. After repeating such procedure twice, the obtained residue was purified by subjecting to silica gel column chromatography [eluent: acetonitrile-methylene chloride (1:9 to 1:4)]to give 0.396 g of (4R,6S)-6-[[(3,5-di-tert-butyl-4-hydroxyphenyl)thio]methyl]-4-hydroxytetrahydropyrane-2-one as crystals (yield: 83%). The desired compound was recrystallized from hexane.

mp: 152°-153° C.

$^1$H-NMR spectrum (in CDCl$_3$) δ ppm: 7.29 (2H, s), 5.28 (1H, s), 4.90-4.74 (1H, m), 4.48-4.37 (1H, m), 3.22 (1H, dd, J=13.6, 4.6 Hz), 2.97 (1H, dd, J=13.6, 7.8 Hz), 2.75 (1H, dd, J=17.8, 4.8 Hz), 2.61 (1H, ddd, J=17.8, 3.8, 1.6 Hz), 2.27 (1H, bd, J=13.6 Hz), 2.10 (1H, b), 1.90-1.72 (1H, m), 1.43 (18H, s)

$[α]_D^{25}$: +27.4±0.7° (c=1.016, methanol)

Elemental analysis value: As C$_{20}$H$_{30}$O$_4$S

Calculated C: 65.54, H: 8.25, S: 8.75

Found C: 65.54, H: 8.19, S: 8.59

EXAMPLE 3

[Sodium (3R,5S)-6-[(3,5-di-tert-butyl-4-hydroxyphenyl)thio]-3,5-dihydroxyhexanoate]

To 1.6 ml of a solution of acetonitrile containing 150 mg (0.409 mmol) of (4R,6S)-6-[[(3,5-di-tert-butyl-4-hydroxyphenyl)thio]methyl]-4-hydroxytetrahydropyrane-2-one was added 0.98 ml of 1N lithium hydroxide with stirring in an atmosphere of argon at −20° C. After 30 minutes thereto was added 3.9 ml of 0.1 M solution of citric acid, and an organic solvent was distilled away under reduced pressure at a temperature not more than 25° C. In ether was dissolved the residue and the mixture was washed with saturated brine solution, dried and distilled away under reduced pressure to give 157 mg of (3R,5S)-6-[(3,5-di-tert-butyl-4-hydroxyphenyl)thio]-3,5-dihydroxyhexanoic acid. Thereto was added 3.9 ml (0.389 mmol) of 0.1 N sodium hydroxide which was ice-cooled, washed with ether and freeze-dried to give 151 mg of the desired compound (yield: 89%).

$^1$H-NMR spectrum (in CD$_3$OD) δ ppm: 7.24 (2H, s), 4.15-3.98 (1H, m), 3.92-3.75 (1H, m), 2.91 (1H, dd, J=14.0, 6.0 Hz), 2.84 (1H, dd, J=14.0, 6.8 Hz),
2.32 (1H, dd, J=15.2, 5.2 Hz), 2.20 (1H, dd,
J=15.2, 7.8 Hz), 1.88-1.40 (2H, m),
1.39 (18H, s) $[\alpha]_D^{24}$: $-7.9\pm0.5°$ (c=1.019, methanol)
Elemental analysis value: As
$C_{20}H_{31}O_5SNa \cdot \frac{1}{2} H_2O$
Calculated C: 57.81, H: 7.76, S: 7.72
Found C: 57.84, H: 7.50, S: 7.84

EXAMPLE 4

[(3R,5R)-Methyl
7-(3,5-di-tert-butyl-4-hydroxy)phenyl-3,5-dihydroxyheptanoate]

A solution of 100 ml of THF and 25 ml of methanol containing 5.91 g (15.6 mmol) of (3R)-methyl-7-(3,5-di-tert-butyl-4-hydroxy)phenyl-3-hydroxy-5-oxo-hexanoate was cooled to $-78°$ C. Thereto was added 17.2 ml of 1 M diethyl methoxy borane. Further thereto was added 650 mg (817.2 mmol) of sodium borohydride. After stirring for 3 hours, thereto was added 15.6 ml of acetic acid and the mixture was extracted with methylene chloride. To the residual solution were added methanol and toluene, and concentration was repeated for several times. The residue was purified by subjecting to silica gel column chromatography [eluent: hexane-ethyl acetate (1:1)] to give 4.76 g of the desired compound (yield: 80%). Rf value thereof was 0.4 (hexane-ethyl acetate (1:1)).

$^1$H-NMR spectrum (in CDC$_3$) δ ppm: 1.43 (18H, s), 1.6-1.8 (4H, m),
2.4-2.8 (4H, m), 3.72 (3H, s), 3.9-4.1 (1H, m), 4.2-4.4 (1H, m), 5.03 (1H, s), 7.00 (2H, s)
$[\alpha]_D^{25}$: $-2.67°$ (c=2.21, CHCl$_3$)

EXAMPLE 5

[Sodium
(3R,5R)-7-(3,5-di-tert-butyl-4-hydroxy)phenyl-3,5-dihydroxy-heptanoate]

A solution of 51 ml of methanol containing 5.11 g (13.4 mmol) of (3R,5R)-methyl 7-(3,5-di-tert-butyl-4-hydroxy)phenyl-3,5-dihydroxy-heptanoate was cooled to 0° C. Thereto was added 16.1 ml of 1 N sodium hydroxide and the mixture was stirred for 3 hours. The reaction solution was concentrated under reduced pressure. The residual solution was purified by subjecting to a column chromatography (MCI® GEL CHP20P, made by MITSUBISHI CHEMICAL INDUSTRIES LTD.) [eluent: 50% methanol] and freeze-dried to give 4.76 g of the desired compound (yield: 80%). Rf value thereof was 0.9 (ethyl acetate-acetic acid-water (30:1:1)).

$^1$H-NMR spectrum (in D$_2$O) δ ppm: 1.04 (18H, s), 1.4-1.6 (4H, m),
1.9-2.4 (4H, m), 3.72 (3H, s), 3.4-3.6 (1H, m), 3.7-3.9 (1H, m), 4.46 (HOD), 6.82 (2H, s)
$[\alpha]_D^{24}$: $+8.3°$ (c=3.31, H$_2$O)
IR (KBr) cm$^{-1}$: 3610, 3390, 2875, 1570, 1430, 1400, 1230, 1155, 1115, 765
Elemental analysis value: As $C_{21}H_{33}O_5Na$ 0.29 H$_2$O
Calculated C: 64.06, H: 8.67, Na: 5.84
Found C: 63.79, H: 8.56, Na: 5.84

EXAMPLE 6

[(3R,5R)-7-(3,5-di-tert-butyl-4-hydroxy)phenyl-3-hydroxy-5-heptanolide]

To a solution of 10 m; of ether containing 667 mg (1.75 mmol) of (3R,5R)-methyl 7-(3,5-di-tert-butyl-4-hydroxy)phenyl-3,5-dihydroxyheptanoate was added 50 mg of p-toluenesulfonic acid monohydrate. To the reaction solution was added toluene, and the mixture was evaporated to dryness for several times. The residual solution was purified by subjecting to silica gel column chromatography [eluent: hexane-ethyl acetate (1:2)] to give 569 mg of the desired compound (yield: 93%). Rf value thereof was 0.4 (hexane-ethyl acetate (1:1)).

$^1$H-NMR spectrum (in CDCl$_3$) δ ppm:
1.43 (18H, s), 1.7-2.1 (4H, m),
2.6-2.9 (4H, m), 4.3-4.5 (1H, m),
4.7-4.9 (1H, m), 5.08 (1H, s), 7.00 (2H, s)

The compounds obtained in Example 3, (hereinafter shown as Compound No. 3) was subjected to the following Bioactivity evaluation.

Bioactivity evaluation

Test Example 1

[HMG-CoA reductase inhibitory activity]

(1a) Preparation of rat liver microsome

Liver microsomes was prepared by using Sprague-Dawley rats which freely take a general diet containing 2% cholestyramine and water for 2 weeks according to the report of Kuroda et al (Biochim. Biophys. Acta., 486, page 70, 1977). The microsome fraction obtained by centrifuging at 105000× g was washed with a solution containing 15 mM nicotinamide and 2 mM magnesium chloride (in 100 mM potassium phosphate buffer solution, pH 7.4) once. Then, thereto was added equal parts of the buffer solution containing nicotinamide and magnesium chloride to the weight of used liver. The mixture was homogenized, cooled to $-80°$ C., and preserved.

(1b) Measurement of HMG-CoA reductase inhibitory activity

At 0° C., 100 μl of rat liver microsome preserved at $-80°$ C. was melted and diluted with 0.7 ml of cool potassium phosphate buffer (100 mM, pH 7.4). Thereto was added 0.8 ml of 50 mM EDTA solution (the above-mentioned potassium phosphate buffer solution) and 0.4 ml of 100 mM dithiothreitol solution (the above-mentioned potassium phosphate buffer solution) and the mixture was maintained at 0° C. To 1.675 ml of the microsome solution was added 670 μl of 25 mM NADPH solution (the above-mentioned potassium phosphate buffer solution). To the solution was added 670 μl of 0.5 mM [3-$^{14}$C]HMG-CoA solution (3 mCi/mmol). To 45 μl of the mixture of the microsome and HMG-CoA was added 5 μl of potassium phosphate buffer solution containing a test compound, the solution was incubated at 37° C. for 30 minutes. After cooling, 10 μl of 2 N hydrochloric acid was added thereto and the solution was again incubated at 37° C. for 15 minutes. After 30 μl of the obtained mixture was applied to silica gel thin-layer chromatography plate (of 0.5 mm thick) (trade number Art 5744, made by Merck AG) and was developed in toluene-acetone (1:1 by volume), a portion having 0.45-0.60 of Rf value was scratched. The scratched portion was added to a vial in which 8 ml of scintillation cocktail was added. By means of a scintillation counter, specific activity was measured.

TABLE 1

| Test compound | HMG-CoA reductase inhibitory activity IC$_{50}$ (50% inhibition concentration) |
| --- | --- |
| Compound No. 3 | 54 μM |
| Lovastatin | 24 nM |

TEXT EXAMPLE 2

[Suppression of production of peroxidized lipids in a homogenate of rat brain]

SD strain rats (body weight, about 200 g) were sacrificed by cutting down their heads, and the brains were taken out. The brains were homogenated with a 4-fold amount of 0.05 M phosphate-sodium chloride buffer (pH 7.4) and centrifuged at 1,000× g for 10 minutes. The supernatant was kept at −80° C. for storage.

The supernatant was diluted with a 2-fold amount of the same phosphate-sodium chloride buffer as above, and 0.45 ml of the dilution was combined with 30 μl of ethanol per se (vehicle) or ethanol solution containing a test compound, followed by incubation at 37° C. for 30 minutes. The reaction was terminated by addition of a solution of 0.1% butylhydroxytoluene (BHT) (20 μl) in 25% metaphosphoric acid (125 μl). After deproteinization, the peroxidized lipids in the supernatant were measured by the thiobarbituric acid (TBA) method according to the description by Ohkawa et al.: in Anal. Biochem., Vol. 95, page 351 (1979). The amount of peroxidized lipids produced was compared with that in the vehicle applied group and expressed in % control. The results are shown in Table 2.

TABLE 2

| Test compound | Concentration of test compound (mM) | Inhibitory rate (% control) |
| --- | --- | --- |
| Compound No. 3 | 0.01 | 35.7 |
|  | 0.1 | 94.9 |
| Probucol | 0.01 | 27.8 |
|  | 0.1 | 58.3 |

In addition to the ingredients used in the Examples, other ingredients can be used in the Examples as set forth in the specification to obtain substantially the same results.

What is claimed is:

1. A 2,4,6-substituted phenol having the formula (I):

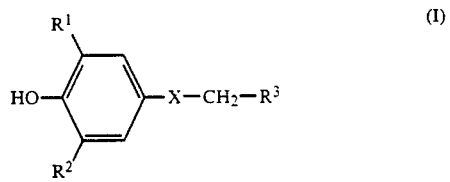

wherein X is S or CH$_2$; R$^1$ and R$^2$ are the same or different from each other and each is a lower alkyl group; R$^3$ is a group represented by the formula:

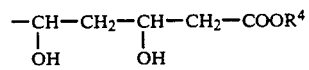

in which R$^4$ is hydrogen atom or a lower alkyl group; or a pharmaceutically acceptable salt thereof.

2. A 2,4,6-substituted phenol according to claim 1, wherein X is S.

3. A 2,4,6-substituted phenol according to claim 1, wherein R$^1$ and R$^2$ are each a branched chain alkyl group.

4. A 2,4,6-substituted phenol according to claim 3, wherein R$^1$ and R$^2$ are each, independently, a branched alkyl selected from the group consisting of isopropyl, isobutyl, sec-butyl, tert-butyl, 1-methylpropyl, isopentyl, neopentyl, tert-pentyl, 1-methylbutyl, 2-methylbutyl, 1,1-dimethylpropyl, 1,1-dimethylbutyl, 2,2-dimethylbutyl and isohexyl.

5. A 2,4,6-substituted phenol according to claim 1, wherein said substituted phenol is in the form of a pharmaceutically acceptable salt with an alkali metal, an alkaline earth metal, an amino acid or an organic amine.

6. A 2,4,6-substituted phenol according to claim 5, wherein said alkali metal is sodium.

7. A 2,4,6-substituted phenol according to claim 1, wherein said substituted phenol is sodium (3R,5S) -6-(3,5-di-tert-butyl-4-hydroxyphenyl) thio)-3,5-dihydroxyhexanoate.

8. A pharmaceutical composition comprising a therapeutically effective amount of a compound claimed in claim 1, as an effective ingredient, in association with a pharmaceutically acceptable substantially nontoxic carrier or excipient.

* * * * *